(12) United States Patent
Rosanoff

(10) Patent No.: US 10,258,646 B2
(45) Date of Patent: Apr. 16, 2019

(54) CREAM TRANSDERMAL MAGNESIUM SUPPLEMENT

(71) Applicant: Andrea Rosanoff, Pahoa, HI (US)

(72) Inventor: Andrea Rosanoff, Pahoa, HI (US)

( * ) Notice: Subject to any disclaimer, the term of this patent is extended or adjusted under 35 U.S.C. 154(b) by 0 days.

(21) Appl. No.: 14/981,455

(22) Filed: Dec. 28, 2015

(65) Prior Publication Data

US 2016/0317576 A1    Nov. 3, 2016

Related U.S. Application Data

(60) Provisional application No. 62/069,345, filed on Oct. 28, 2014.

(51) Int. Cl.
| | | |
|---|---|---|
| *A61K 9/00* | (2006.01) | |
| *A61K 33/14* | (2006.01) | |
| *A61K 47/14* | (2017.01) | |
| *A61K 47/36* | (2006.01) | |
| *A61K 9/107* | (2006.01) | |

(52) U.S. Cl.
CPC ............ *A61K 33/14* (2013.01); *A61K 9/0014* (2013.01); *A61K 9/107* (2013.01); *A61K 47/14* (2013.01); *A61K 47/36* (2013.01)

(58) Field of Classification Search
CPC ........ A61K 33/14; A61K 47/14; A61K 47/36; A61K 9/0014; A61K 9/107
See application file for complete search history.

(56) References Cited

U.S. PATENT DOCUMENTS

| 4,335,103 A | * | 6/1982 | Barker | ..................... A61K 8/03 |
| | | | | 424/59 |
| 2002/0001599 A1 | * | 1/2002 | Neubourg | .............. A61K 8/046 |
| | | | | 424/400 |
| 2005/0276829 A1 | * | 12/2005 | Stella | ................... A61K 8/0291 |
| | | | | 424/401 |
| 2009/0017147 A1 | * | 1/2009 | Lintner | .................. A61K 8/975 |
| | | | | 424/780 |

* cited by examiner

*Primary Examiner* — Aradhana Sasan
(74) *Attorney, Agent, or Firm* — Steven R. Gray; Holland & Hart LLP

(57) ABSTRACT

A transdermal cream composition and related method of creating the formulation includes: magnesium chloride, water, hydroxypropyl starch phosphate, at least one of cetearyl olivate and sorbitan olivate, isopropyl palmitate, emulsifying wax, cetyl alcohol, glycerin, *Butyrospermum parkii* (shea butter). The composition also includes at least one of: iodopropynyl butylcarbamate, phenoxyethanol, caprylyl glycol, benzyl alcohol, benzoic acid, and sorbic acid.

20 Claims, 2 Drawing Sheets

CREAM TRANSDERMAL MAGNESIUM SUPPLEMENT

CROSS-REFERENCE TO RELATED APPLICATION

The present application claims the benefit of U.S. Provisional Application No. 62/069,345, filed on 28 Oct. 2014, which application is incorporated herein in its entirety by this reference.

BACKGROUND

Optimally, the levels of magnesium and calcium in a human body are in a balanced state. Magnesium functions physiologically in the body to control nerve action, heart activity, neuromuscular transmission, muscular contraction, vascular tone, blood pressure, and peripheral blood flow. Magnesium regulates the entry and release of calcium from cells which is determinative of muscular activity. When cells lack sufficient magnesium to balance calcium, it is harder for cells to relax, resulting in a stressed state. When there is insufficient magnesium in muscle cells, in particular, the calcium may cause the muscle cells to contract, resulting in muscle cramps.

Deficiency of magnesium generally can not only cause muscle cramps, but has also been implicated in the pathogenesis of various clinical imbalances, disorders, and/or harmful conditions, including weakness, fatigue, cardiac arrhythmia, respiratory arrest, increased irritability of the nervous system with tremors, anxiety and panic attacks, asthma, blood clots, bowel disease, cystitis, depression, detoxification, diabetes, heart disease, hypertension, hypoglycemia, insomnia, kidney disease, migraines, musculoskeletal conditions, nerve problems, obstetrical and gynecological problems, osteoporosis, Raynaud's syndrome, tooth decay, athetosis, jerking, nystagmus, disorientation, hallucinations, depression, epileptic fits, hypertension, tachycardia, tetany and in extreme cases, even death. Magnesium deficiency can also lead to a disruption of the body's electrolytes, which may be a condition known as hypomagnesemia.

Despite the harmful symptoms of magnesium deficiency, many persons do not receive the recommended daily magnesium requirement-320 mg for women and 400 mg for men. Rather, magnesium intake for the majority of people is apparently between 175 mg and 225 mg per day.

Magnesium deficiency and hypomagnesemia is particularly common among patients in hospitals. Chronic diarrhea, malabsorption, alcoholism, chronic stress, and use of medications such as diuretics may lead to magnesium deficiency. In addition, magnesium deficiency can be the result of a diet lacking magnesium. For example, common nutritional sources of magnesium are green leafy vegetables, legumes, nuts, seeds, and whole grains-foods that have been increasingly rare in diets consisting of large quantities of processed foods.

Oral magnesium supplements are often absorbed by the body at lower-than-desired rates. This is partly the result of the fact that the magnesium found in such oral supplements must pass through the digestive system before circulating to the rest of the body, and often ends up released from the body prior to circulation—via the kidneys, bowel excretion, and due to not being effectively absorbed by the intestines. Oral magnesium supplements may also result in undesired gastrointestinal side effects such as nausea, mild abdominal cramping, loose stools or diarrhea.

These undesirable symptoms of oral magnesium supplements may occur in some people at low levels of oral magnesium supplementation. The upper limit-defined as the lowest amount of a nutrient given as a supplement that will cause any symptoms—of magnesium supplement is generally 350 mg and lower than the male recommended daily allowance. Thus it is desirable to have non-oral magnesium supplements, which that bypass the problems associated with magnesium passing through the gastro-intestinal tract. Although magnesium may be injected into the body, many prefer a less invasive and more convenient method of delivery.

In addition, prior art transdermal magnesium supplements, for example—those in the form of liquids, oils, and/or gels, may not be attractively convenient methods of application. Rather, such prior art transdermal supplements may be messy, sticky, oily, leave a residue on the skin, rub off on clothes, and require persons to wait for prolonged periods for the supplement to dry or evaporate before being able to place clothing over the treated portions of skin. In addition, regardless of other desirable qualities that a prior art transdermal magnesium supplement might possess, it nevertheless might present certain disadvantages due to real or perceived inconvenience associated with its form as an oil, gel, or other liquid (or pseudo-liquid).

Furthermore, in prior art cream transdermal magnesium supplements, the cream and liquid elements of the prior art composition may lack adequate viscosity, and be therefore more prone to separation, thus making application of the substances less attractive. Moreover, prior art magnesium supplements may be designed to increase the global level of magnesium in a body, rather than focus on alleviating pain in certain localized areas of the body, by providing needed magnesium supplement foremost to those localized areas.

SUMMARY

One aspect of the present disclosure relates to a transdermal cream composition that includes: magnesium chloride, water, hydroxypropyl starch phosphate, at least one of cetearyl olivate and sorbitan olivate, isopropyl palmitate, emulsifying wax, cetyl alcohol, glycerin, *Butyrospermum parkii* (shea butter). The composition also includes at least one of: iodopropynyl butylcarbamate, and phenoxyethanol and caprylyl glycol, or benzyl alcohol, benzoic acid, and sorbic acid.

The magnesium chloride may be provided in an amount of about 20 wt. % to 30 wt. %. The magnesium chloride is provided in an amount of about 10 wt. %. The water may be provided in an amount of about 57 wt. % to about 81 wt. %. The at least one of cetearyl olivate and sorbitan olivate may be provided in an amount of about 4 wt. % to about 6 wt. %. The isopropyl palmitate may be provided in an amount of about 4 wt. % to about 6 wt. %. The emulsifying wax may be provided in an amount of about 2.5 wt. % to about 3.5 wt. %. The glycerin may be provided in an amount of about 2.5 wt. % to about 3.5 wt. %. The *Butyrospermum parkii* (shea butter) may be provided in an amount of about 0.7 wt. % to about 1.3 wt. %. The hydroxypropyl starch phosphate may be provided in an amount of about 0.8 wt. % to about 1.2 wt. %. The iodopropynyl butylcarbamate may be provided in an amount of about 0.08 wt. % to about 0.12 wt. %. The phenoxyethanol and caprylyl glycol may be provided in an amount of about 0.7 wt. % to about 1.3 wt. %.

Another aspect of the present disclosure relates to a transdermal cream composition that includes magnesium chloride, at least one diluent, at least one emulsifier, and at least one fat soluble component. The magnesium chloride may be provided in an amount of about 10% wt. The transdermal cream composition may also include at least one modifier, at least one thickener, at least one emollient, at least one humectant, and at least one preservative.

The at least one diluent may include water. The at least one emulsifier may include at least one of cetearyl olivate and sorbitan olivate. The at least one fat soluble component may include *Butyrospermum parkii* (shea butter). The at least one modifier may include hydroxyl starch phosphate. The at least one thickener may include cetyl alcohol. The at least one emollient may include isopropyl palmitate. The at least one humectant may include glycerin. The at least one preservative may include one of: iodopropynyl butylcarbamate, and phenoxyethanol and caprylyl glycol, or benzyl alcohol, benzoic acid and sorbic acid.

Another aspect of the present disclosure relates to a method of forming a transdermal cream composition. The method includes dissolving magnesium chloride and hydroxyl starch phosphate in a first volume of water to form a first mixture, mixing cetearyl olivate, sorbitan olivate, cetyl alcohol and emulsifying wax in a second volume of water to form a second mixture, heating the second mixture, after heating the second mixture, cooling the second mixture and combining the first and second mixtures together to form a third mixture, and adding isopropyl palmitate, glycerin, *Butyrospermum parkii* (shea butter) and at least one of iodopropynyl butylcarbamate, and phenoxyethanol and caprylyl glycol, or benzyl alcohol, benzoic acid, and sorbic acid to the third mixture to form the transdermal cream composition. Heating the second mixture may include heating to a temperature of about 85° C. Cooling the second mixture may include reducing the temperature to about 45° C.

The above summary is not intended to describe each embodiment or every implementation of embodiments of the present disclosure. The Figures and the detailed description that follow more particularly exemplify one or more preferred embodiments.

BRIEF DESCRIPTION OF THE FIGURES

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

Figure 1:
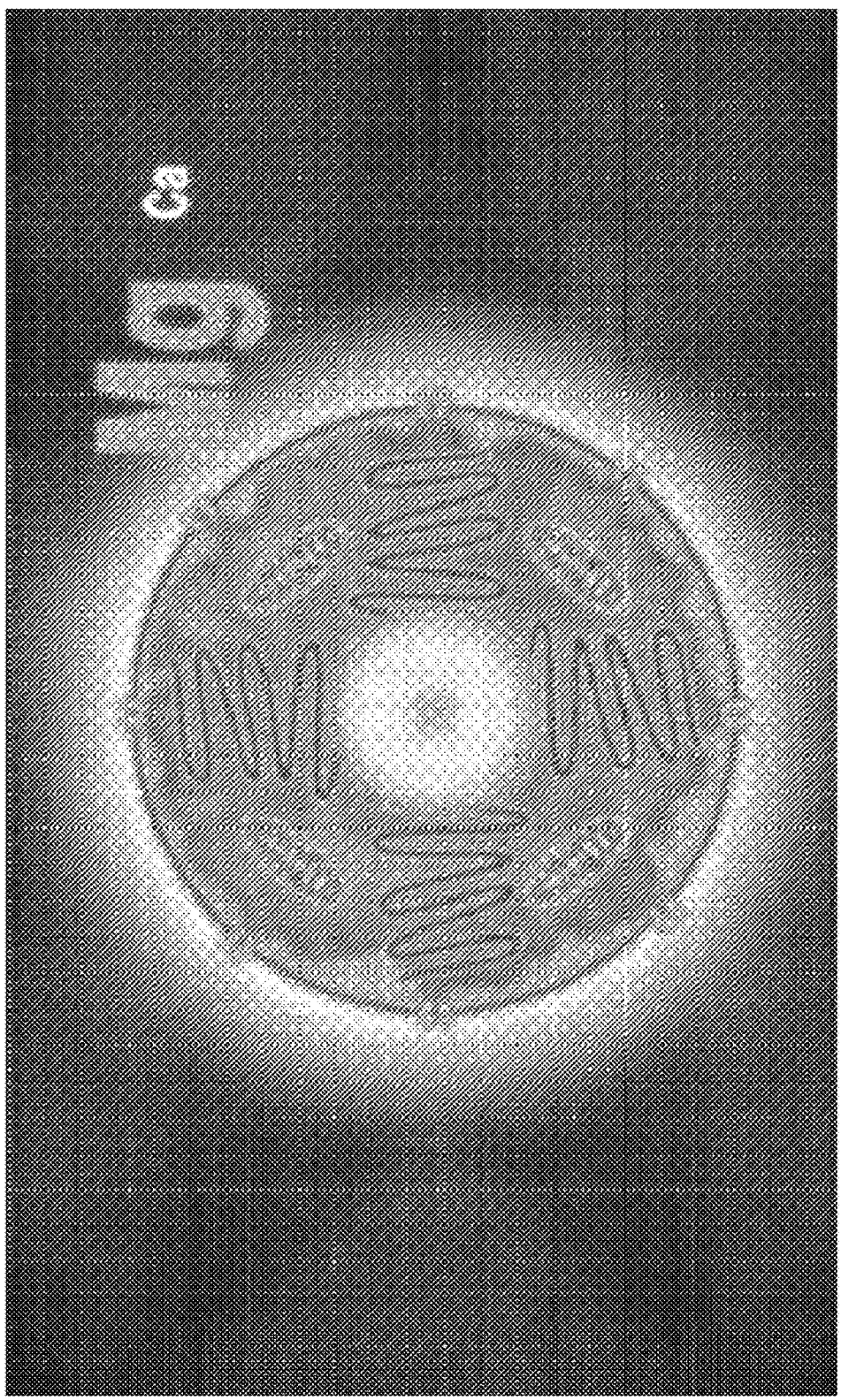
FIG. 1 is an illustration of a cell where levels of calcium and magnesium are balanced.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

The present disclosure relates to transdermal magnesium supplement in the form of cream, which may deliver magnesium into the human tissues. The magnesium may assist in, for example, alleviating localized pain symptoms of magnesium deficit in muscle/nerves and other tissues. Transdermal delivery of magnesium supplement via a cream may be more effective and avoid many of the harmful side effects associated with oral magnesium supplements. Transdermal delivery of magnesium supplement via a cream may also be safer, more convenient, less painful, and more patient friendly than injections or intravenous therapy, thus improving patient compliance.

Embodiments of the cream transdermal magnesium supplement described herein may be more convenient and not possess some of the undesirable qualities (and/or perceived undesirable qualities) associated with prior transdermal magnesium supplements, such as leaving a residue, and/or having an unattractive texture or sensation against the skin. Rather, when compared with prior transdermal supplements, the compositions described herein may have a surprisingly pleasant texture, may be absorbed quickly into the skin, and may dry or evaporate more quickly from a skin surface, may be less sticky, and may leave less of a residue on the skin. Furthermore, the compositions disclosed herein may include a cream transdermal magnesium supplement having more optimal viscosity than other cream transdermal magnesium supplements, wherein the cream and liquid elements of the prior compositions may be more prone to separation, and thus may have methods of application that are less convenient and comfortable. Prior compositions of transdermal magnesium supplements have not adequately carried sufficient magnesium while maintaining a lotion texture that makes application sufficiently soothing, easy, and attractive.

Qualities of the composition described herein may have the surprising result of persons with magnesium deficiency using the cream transdermal magnesium supplement more frequently and regularly than prior art supplements, which may lead to more effective treatment. Furthermore, although it is anticipated that embodiments of the cream transdermal magnesium supplement will have high levels of magnesium chloride, or similar ingredient, it may be the case that, due to its convenience and comfortable method of application, the cream transdermal magnesium supplement may be even more effective in treating magnesium deficiency than prior art transdermal solutions with a conceivably higher concentration of magnesium. This result may be somewhat surprising since one might normally expect a solution with a higher concentration of magnesium to be more effective in treating magnesium deficiency.

Moreover, the cream transdermal magnesium supplement, an embodiment of which is described herein, may alleviate localized pain in an effective manner, by such application and reapplication to those localized areas of the body suffering pain and/or discomfort, due to localized magnesium deficit in muscle, nerve or connective tissue cells. This surprisingly effective pain relief may be due, at least in part, to the composition of certain embodiments, which may provide a high level of permeability, allowing the solution, and in particular the magnesium of the supplement, to be absorbed through the skin. An additional advantage of this cream composition and method of application is that a person may control how large of doses to apply according to user preference and according to level and location of pain.

One embodiment of the cream transdermal magnesium supplement described herein may contain some or all of (but not limited to) the following ingredients and equivalents thereof: magnesium chloride, aqua (water), cetearyl olivate, sorbitan olivate, cetyl alcohol, isopropyl palmitate, emulsifying wax, glycerin, *Butyrospermum parkii* (shea butter), hydroxypropyl starch phosphate, and one or more of iodopropynyl butylcarbamate, phenoxyethanol, caprylyl glycol, benzyl alcohol, benzoic acid and sorbic acid. One embodiment may contain one or more of iodopropynyl butylcarbamate, and phenoxyethanol and caprylyl glycol, or benzyl alcohol, benzoic acid and sorbic acid. It is anticipated that a number of emulsifiers, fat soluble components such as moisturizers, thickeners, emollients, humectants, preservatives, and combinations thereof could be used to attain a cream form that does not separate under typical environmental conditions and provides transfer of magnesium through the skin. In some embodiments, the cream may have a smooth creamy texture.

Furthermore, depending on the embodiment, the percentage of magnesium chloride may vary. In certain embodiments, for example the percentage may be as much as the composition will allow. In other embodiments, the percentage may be about 10%. Although it is anticipated that the cream transdermal magnesium supplement may have broad applications in a number of circumstances and for persons in a variety of situations, embodiments thereof may have specific application for those experiencing muscle cramps or inflammation in certain localized areas, and also for hospital patients.

Also claimed herein, and described more fully in the description section below, is a method for making such a cream/lotion of transdermal magnesium supplement. In addition, as described in more detail in the examples below, some embodiments may include ingredients that are less likely to have harmful side effects than other potential ingredients.

Referring to the figures, FIG. 1 shows a cell where the levels of magnesium in the cell are sufficient to maintain a desirable balance with the calcium (shown in white), and to keep the calcium on the outside of the cell (or properly sequestered within the cell).

Figure 2:
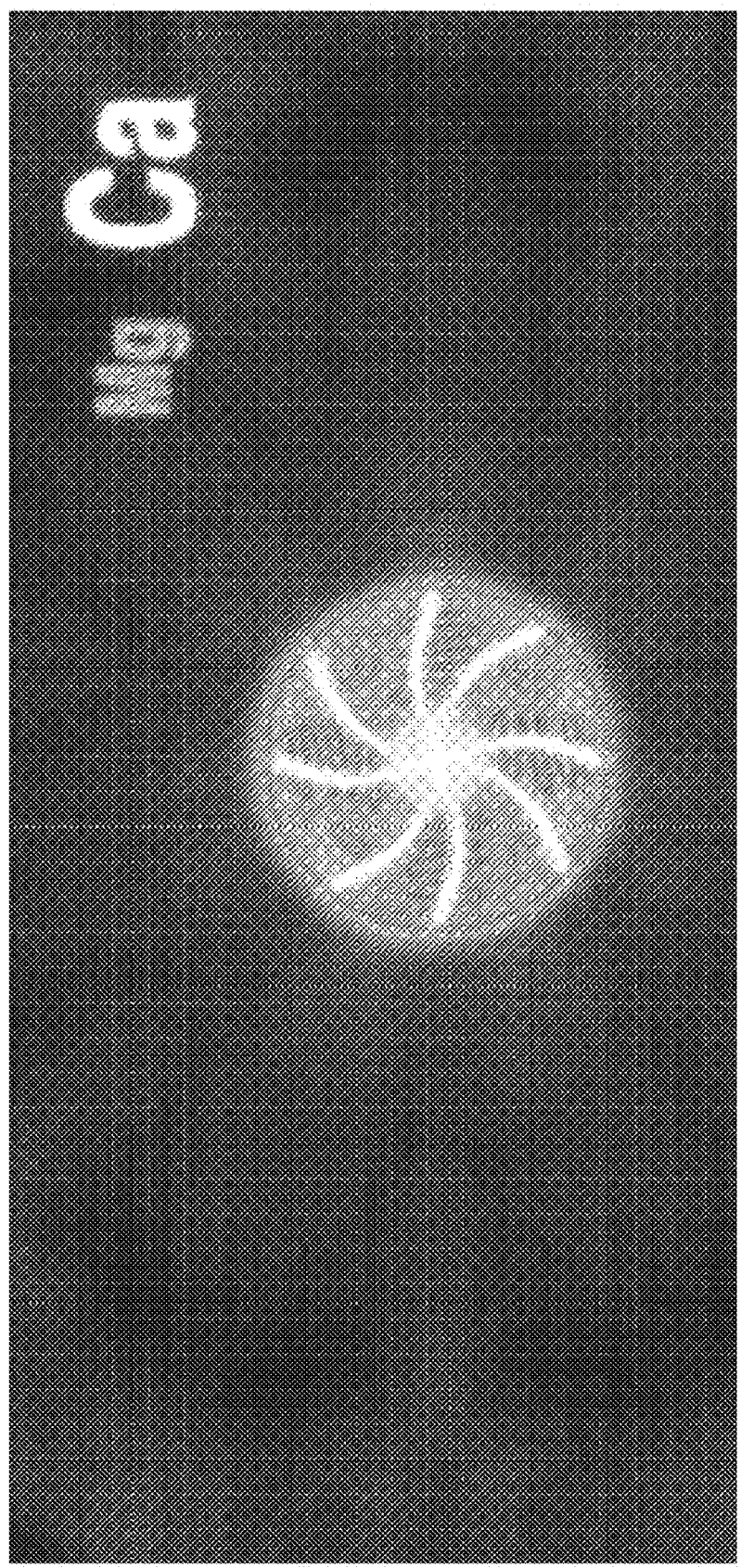
FIG. 2 is an illustration of the cell of FIG. 1 where calcium has entered the cell because there is a deficient level of magnesium.

FIG. 2 shows a cell in a state where the calcium (shown in white) has entered the cell, causing the cell to be in a state of stress and to contract. The cell is less able to relax where there are insufficient levels of magnesium to force the calcium back out of the cell (or into sequestration), causing the cell to be in a constantly stressed state. Where the cream transdermal magnesium supplement is applied, however, to a localized area of the body suffering from such a state due to magnesium deficiency, the appropriate balance between calcium and magnesium is able to return, and the cell may return to a more relaxed state where the calcium is outside the cell (or in sequestration), as shown in FIG. 1 thus leading to less pain.

Various forms of magnesium may be used according to the embodiments disclosed herein. Magnesium chloride is particularly effective at transferring through the skin while also being relatively comfortable when applied to a person's skin. Testing was conducted on a number of magnesium chloride compositions to determine effectiveness for the resulting transdermal cream composition to: 1) transfer magnesium through the skin, 2) provide comfort when applying the cream to a person's skin, and 3) maintain coalescence as a cream composition without separating. The following example formulations and/or compositions provide the desired objectives. These compositions, when created according to the procedural steps and other notes provided after the listing of components of the composition, were found to be particularly effective in meeting the objectives noted above.

Example 1—Magnesium Cream

| | INCI Name | Trade Name or Common Name | Weight % | Functional Name |
|---|---|---|---|---|
| 1. | Aqua I | Water | 25.0 | Diluent |
| 2. | Magnesium Chloride | Magnesium Chloride | 10.0 | Active Rheology |
| 3. | Hydroxy Starch Phosphate | Structure XL | 1.0 | Modifier |
| 4. | Aqua II | Water | 43.9 | Diluent |
| 5. | Cetearyl Olivate and Sorbitan Olivate | Olivem 1000 | 5.0 | Emulsifier |
| 6. | Cetyl Alcohol | Kalcol 6098 | 2.0 | Thickener |
| 7. | Emulsifying Wax | Polawax | 3.0 | Emulsifier |
| 8. | Isopropyl Palmitate | Isopropyl Palmitate | 5.0 | Emollient |
| 9. | Glycerin | Glycerin | 3.0 | Humectant |
| 10. | *Butyrospermum Parkii* (shea butter) | Lipex 205 | 1.0 | Moisturizer |
| 11. | Phenoxyethanol and Caprylyl Glycol | Optiphen | 1.0 | Preservative |
| 12. | Iodopropynyl Butylarbamate | Liquagard (10% IPBC) | 0.1 | Preservative |
| | | | 100.00 | |

Procedure Steps

Dissolve components 2 and 3 in component 1 (water) at room temperature and mix and set aside Add components 5, 6, 7 to component 4 (water) and heat to about 85° C. with mixing Reduce temperature to about 45° C. while mixing and add mixture from step 1

Add 8, 9, 10, 11, 12 with continuous mixing between additions while further cooling Example 2—Magnesium Cream with Ecocert Preservative

| | INCI Name | Trade Name or Common Name | Weight % | Functional Name |
|---|---|---|---|---|
| 1. | Aqua I | Water | 25.0 | Diluent |
| 2. | Magnesium Chloride | Magnesium Chloride | 10.0 | Active Rheology |
| 3. | Hydroxy Starch Phosphate | Structure XL | 1.0 | Modifier |
| 4. | Aqua II | Water | 44.0 | Diluent |
| 5. | Cetearyl Olivate and Sorbitan Olivate | Olivem 1000 | 5.0 | Emulsifier |
| 6. | Cetyl Alcohol | Kalcol 6098 | 2.0 | Thickener |
| 7. | Emulsifying Wax | Polawax | 3.0 | Emulsifier |
| 8. | Isopropyl Palmitate | Isopropyl Palmitate | 5.0 | Emollient |
| 9. | Glycerin | Glycerin | 3.0 | Humectant |
| 10. | *Butyrospermum parkii* (shea butter) | Lipex 205 | 1.0 | Moisturizer |
| 11. | Benzyl Alcohol and Glycerin and Benzoic acid and Sorbic acid | Optiphen BSB-N | 1.0 | Preservative |
| | | | 100.0 | |

Procedure Steps

Dissolve components 2 and 3 in component 1 (water) at room temperature and mix and set aside Add components 5, 6, 7 to component 4 (water) and heat to about 85° C. with mixing Reduce temperature to about 45° C. while mixing and add mixture from step 1

Add 8, 9, 10, 11 with continuous mixing between additions while further cooling

Note: The pH of the final product should be 5.4 or below, preferably around 5.0. Citric acid may be needed to adjust the pH.

The ingredients: Aqua I and II in Examples 1 and 2 are typically the same type of water that is used to mix with other ingredients of the composition during various stages of the procedural steps for each composition.

The weight % amounts for the ingredients of Examples 1 and 2 may be provided within a range of values as shown in Table I below. Each value within each range may be used with the compositions of Examples 1 and 2 to provide the desired outcomes. Varying the amount of one of the ingredients within the given range may result in the need to increase or decrease the amount of one or more of the other ingredients. Some specific variations of ingredients are contemplated depending on the choice of preservative(s). For example, depending on the preservative, instead of using benzyl alcohol and glycerin and benzoic acid and sorbic acid, one embodiment contemplates using phenoxyethanol and caprylyl glycol, and iodopropynyl butylcarbamate (in the ranges provided below).

TABLE I

INGREDIENT RANGES

| Ingredient | Wt % | Lower Limit | Upper Limit |
| --- | --- | --- | --- |
| Aqua | 25.0 | 20.0 | 30.0 |
| Magnesium Chloride | 10.0 | 8.0 | 12.0 |
| Hydroxypropyl Starch phosphate | 1.0 | 0.8 | 1.2 |
| Aqua | 44.0 | 37.0 | 51.0 |
| Cetearyl Oliate and Sorbitan olivate | 5.0 | 4.0 | 6.0 |
| Cetyl Alcohol | 2.0 | 1.5 | 3.0 |
| Emulsifying Wax | 3.0 | 2.5 | 3.5 |
| Isopropyl Palmitate | 5.0 | 4.0 | 6.0 |
| Glycerin | 3.0 | 2.5 | 3.5 |
| *Butyrospermum parkii* (shea butter) | 1.0 | 0.7 | 1.3 |
| Benzyl Alcohol and Glycerin and Benzoic acid and Sorbic acid | 1.0 | 0.9 | 1.5 |
| Phenoxyethanol and Caprylyl Glycol | 1.0 | 0.7 | 1.3 |
| Iodopropynyl Butylarbamate | 0.1 | 0.08 | 0.12 |

The temperatures used in the procedural steps for creating the compositions of Examples 1 and 2 may vary depending on a variety of factors. The temperature for heating up the mixtures of ingredients 4-7 may be in the range of about 70° C. to about 100° C. The temperature range for cooling the mixture of ingredients 4-7 after heating up is in the range of about 30° C. to about 60° C.

Many other compositions are possible using combinations of ingredients of Examples 1 and 2, alone or in combination with other ingredients. Generally, the compositions include magnesium chloride, a diluent, an emulsifier, and a water soluble fat such as the moisturizers included in Examples 1 and 2. An example emulsifier is Versagel from Calumet, the Versagel M 500 product is white mineral oil, CAS RN=8042-47-5. Versagel M 200, 750 and 1600 are mixtures. Another example composition, with ingredient amounts provided to make 100 g Magnesium cream includes:

10 g $MgCl_2$-6 $H_2O$
2 g Versagel
Procedural Steps
  Mix ingredients
  Add a moisturizer such as *Butyrospermum parkii* (shea butter) in an amount to make 100 g total and mix.

$MgCl_2$-6 $H_2O$ is pharmaceutical grade and purchased from Sigma-Aldrich. Various weights of Versagels are possible: 200, 500, 750 and 1600. This composition provided for magnesium chloride in an amount of about 12,000 ppm. The *Butyrospermum parkii* (also referred to as "B-Cream" or "shea butter") may be provided by Gallipot, Inc. and described as:

a petrolatum and glycerin free cream base; A petrolatum-free oil-in-water emulsion base for incormation of various active ingredients. Caution: For prescription compounding. Contains: Purified Water, Cetyl Alcohol, Propylene Glycol, Sodium Laury Sulfate, White Beeswax, Methylparaben and Propylparaben.

Other similar compositions are possible, such as those that include a higher concentration of magnesium chloride. An example high magnesium chloride composition includes:

20 g $MgCl_2$-6 $H_2O$
2 g Versagel
Procedural Steps
  Mix ingredients
  Add a moisturizer such as *Butyrospermum parkii* (shea butter) in an amount to make 100 g total and mix.

In some examples, some lite-salt such as NaCl+KCl, or NuSalt (KCl) is added to promote a gel phase in gel/sol mixtures.

The present description provides examples, and is not limiting of the scope, applicability, or configuration set forth in the claims. Thus, it will be understood that changes may be made in the function and arrangement of elements discussed without departing from the spirit and scope of the disclosure, and various embodiments may omit, substitute, or add other procedures or components as appropriate. For instance, the methods described may be performed in an order different from that described, and various steps may be added, omitted, or combined. Also, features described with respect to certain embodiments may be combined in other embodiments.

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

What is claimed is:

1. A method of forming a magnesium supplement transdermal cream composition, comprising:
   dissolving magnesium chloride and a rheology modifier in a first volume of water to form a first mixture;
   mixing a first emulsifier, a thickener and a second emulsifier distinct from the first emulsifier in a second volume of water to form a second mixture;
   heating the second mixture;
   after heating the second mixture, cooling the second mixture and combining the first and second mixtures together to form a third mixture;

after forming the third mixture, adding an emollient, a humectant, a moisturizer distinct from magnesium chloride and at least one preservative to the third mixture to form the magnesium supplement transdermal cream composition, the magnesium supplement transdermal cream composition having a smooth creamy texture.

2. The method of claim 1, wherein the rheology modifier comprises hydroxyl starch phosphate.

3. The method of claim 1, wherein the first emulsifier comprises at least one of cetearyl olivate or sorbitan olivate.

4. The method of claim 1, wherein the thickener comprises cetyl alcohol.

5. The method of claim 1, wherein the second emulsifier comprises emulsifying wax.

6. The method of claim 1, wherein the dissolving occurs at about room temperature.

7. The method of claim 1, wherein at least some of the mixing occurs as the second mixture is heating.

8. The method of claim 1, wherein the heating comprises heating the second mixture to about 85° C.

9. The method of claim 1, wherein at least some of the mixing the second mixture occurs as the second mixture is cooling.

10. The method of claim 1, wherein the cooling comprises reducing the temperature to about 45° C.

11. The method of claim 10, wherein at least some of the mixing the second mixture occurs after the second mixture is cooled to about 45° C.

12. The method of claim 1, wherein at least some of the combining the first mixture and the second mixture occurs as the second mixture is cooling.

13. The method of claim 1, wherein the emollient comprises isopropyl palmitate.

14. The method of claim 1, wherein the humectant comprises glycerine.

15. The method of claim 1, wherein the moisturizer comprises *Butyrospermum parkii* (shea butter).

16. The method of claim 1, wherein the least one preservative comprises at least a first preservative and a second preservative distinct from the first preservative, and the first preservative comprises at least one of phenoxyethanol or caprylyl glycol, and the second preservative comprises iodopropynyl butylcarbamate.

17. The method of claim 1, wherein the at least one preservative comprises at least one of benzyl alcohol, glycerin, benzoic acid or sorbic acid.

18. The method of claim 10, wherein the adding comprises adding the emollient, the humectant, the moisturizer, and the at least one preservative each separately, with at least some mixing between each addition.

19. The method of claim 18, further comprising cooling during the adding from less than 45° C. to about room temperature.

20. The method of claim 1, further comprising adjusting pH below 5.5 for the transdermal cream composition.

* * * * *